(12) United States Patent
Rogers et al.

(10) Patent No.: US 9,969,897 B2
(45) Date of Patent: May 15, 2018

(54) PROCESS TO PRODUCE AN AQUEOUS DISPERSION, AN AQUEOUS DISPERSION PRODUCED THEREBY AND A COATING COMPOSITION COMPRISING THE AQUEOUS DISPERSION

(71) Applicants: Dow Global Technologies LLC, Midland, MI (US); Union Carbide Chemicals & Plastics Technology LLC, Midland, MI (US); Rohm and Haas Company, Philadelphia, PA (US)

(72) Inventors: True L. Rogers, Midland, MI (US); Aslin Izmitli, Yardley, PA (US); Susan L. Jordan, Doylestown, PA (US); David L. Malotky, Midland, MI (US); Shari L. Workentine, Midland, MI (US); Kebede Besbah, Harleysville, PA (US)

(73) Assignees: ROHM AND HAAS COMPANY, Philadelphia, PA (US); DOW GLOBAL TECHNOLOGIES LLC, Midland, MI (US)

( * ) Notice: Subject to any disclaimer, the term of this patent is extended or adjusted under 35 U.S.C. 154(b) by 13 days.

(21) Appl. No.: 14/914,366

(22) PCT Filed: Aug. 25, 2014

(86) PCT No.: PCT/US2014/052500
§ 371 (c)(1),
(2) Date: Feb. 25, 2016

(87) PCT Pub. No.: WO2015/031244
PCT Pub. Date: Mar. 5, 2015

(65) Prior Publication Data
US 2016/0208126 A1      Jul. 21, 2016

Related U.S. Application Data

(60) Provisional application No. 61/871,539, filed on Aug. 29, 2013.

(51) Int. Cl.
C09D 101/00      (2006.01)
A61K 9/10         (2006.01)
(Continued)

(52) U.S. Cl.
CPC ............ *C09D 101/28* (2013.01); *A23P 20/10* (2016.08); *A23P 20/105* (2016.08); *A23P 30/20* (2016.08);
(Continued)

(58) Field of Classification Search
None
See application file for complete search history.

(56) References Cited

U.S. PATENT DOCUMENTS 4,123,403 A * 10/1978 Warner .................. C08J 3/03
                                                           523/313
4,502,888 A    3/1985 Leng et al.
(Continued)

FOREIGN PATENT DOCUMENTS

EP          0113443       *  7/1984

OTHER PUBLICATIONS

Vsey, et al., "The Influence of Plasticizer Type on the Film Properties of a Fully-Formulated Aqueous Ethylcellulose Dispersion," cOLORCON, AAPS Annual Meeting, (2008).
(Continued)

*Primary Examiner* — Melvin C Mayes
*Assistant Examiner* — Colette Nguyen
(74) *Attorney, Agent, or Firm* — Carl P. Hemenway

(57) ABSTRACT

A process to produce a dispersion comprising feeding ethylcellulose polymer and a dispersant into a melt and mix
(Continued)

zone of an extruder wherein the ethylcellulose polymer and dispersant are melted and mixed together to form a melt; conveying the melt to an emulsification zone of the extruder in which the temperature and pressure are controlled; feeding a base and water into the emulsification zone wherein the melt is dispersed to form a high internal phase emulsion; conveying the emulsion to a dilution and cooling zone of the extruder; and feeding water into the dilution and cooling zone to dilute the high internal phase emulsion thereby forming an aqueous dispersion is provided.

16 Claims, 1 Drawing Sheet

(51) Int. Cl.
| | |
|---|---|
| *C09D 101/28* | (2006.01) |
| *C08J 3/03* | (2006.01) |
| *C08J 3/05* | (2006.01) |
| *C08K 5/09* | (2006.01) |
| *C08K 5/103* | (2006.01) |
| *C08K 5/11* | (2006.01) |
| *A61K 9/50* | (2006.01) |
| *A61K 31/4402* | (2006.01) |
| *A61K 9/28* | (2006.01) |
| *A23P 20/10* | (2016.01) |
| *A23P 30/20* | (2016.01) |
| *C08K 5/00* | (2006.01) |

(52) U.S. Cl.
CPC .............. *A61K 9/10* (2013.01); *A61K 9/2866* (2013.01); *A61K 9/5078* (2013.01); *A61K 31/4402* (2013.01); *C08J 3/03* (2013.01); *C08J 3/05* (2013.01); *C08K 5/0016* (2013.01); *C08K 5/09* (2013.01); *C08K 5/103* (2013.01); *C08K 5/11* (2013.01); *A23V 2002/00* (2013.01); *C08J 2301/28* (2013.01)

(56) References Cited

U.S. PATENT DOCUMENTS

| | | | | |
|---|---|---|---|---|
| 4,960,814 | A * | 10/1990 | Wu | ........................ A61K 8/06 106/163.01 |
| 5,025,004 | A * | 6/1991 | Wu | ........................ A61K 8/06 106/170.12 |
| 5,539,021 | A | 7/1996 | Pate et al. | |
| 5,756,659 | A | 5/1998 | Hughes et al. | |
| 2012/0029132 | A1 | 2/2012 | Moncla et al. | |
| 2013/0101847 | A1 | 4/2013 | Neubauer et al. | |

OTHER PUBLICATIONS

Wagner, "Improvement of the Low-Temperature Stability of an Aqueous Colloidal Ethylcellulose Dispersion, Aquacoat ECD, and Preparation/Characterization of a Redispersible Aquacoat ECD Powder", J. Drug Development and Industrial Pharmacy, vol. 29, No. 3, pp. 267-275 (2003).

Heng, et al., "Influence of storage conditions and type of plasticizers on ethylcellulose and acrylate films formed from aqueous dispersions", J. Pharm Pharmaceut Sci, vol. 6, No. 3, pp. 334-344 (2003).

* cited by examiner

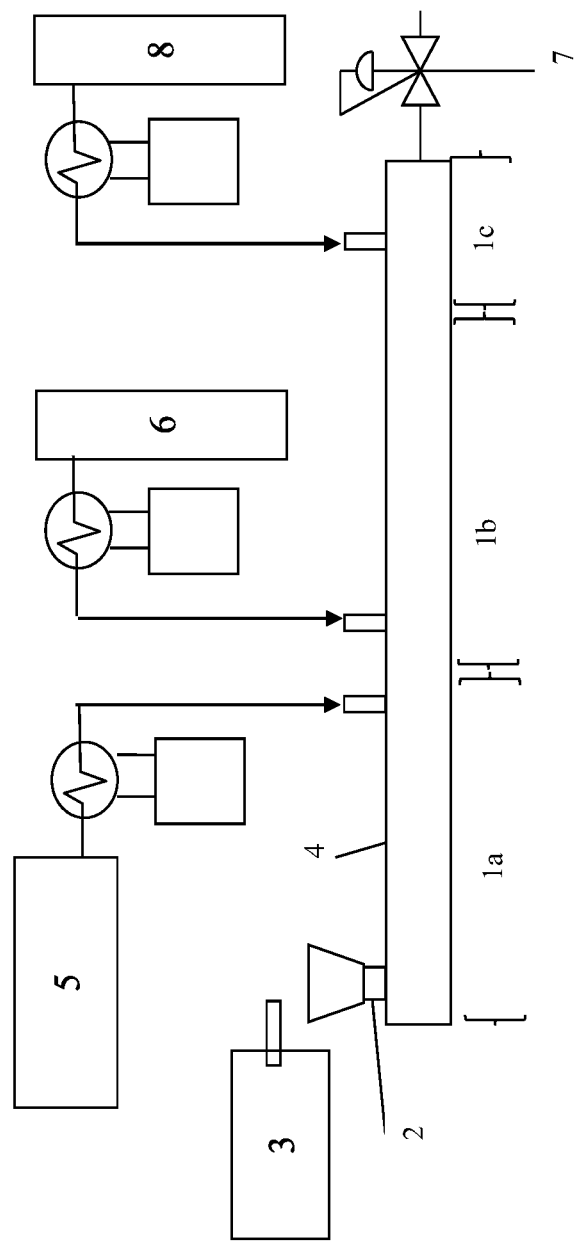

PROCESS TO PRODUCE AN AQUEOUS DISPERSION, AN AQUEOUS DISPERSION PRODUCED THEREBY AND A COATING COMPOSITION COMPRISING THE AQUEOUS DISPERSION

FIELD OF INVENTION

The instant invention relates to a process to produce an aqueous dispersion, an aqueous dispersion produced thereby, a pharmaceutical coating composition and a food coating composition comprising the aqueous dispersion.

BACKGROUND OF THE INVENTION

Coating compositions currently made from dispersions mechanically produced in an aqueous medium using ethylcellulose as a base polymer typically have pH of greater than 10. Such high pH arises from the use of ammonia to prevent coagulation of the dispersion. Ammonia odors, however, give rise to health concerns for coating applicators and require the use of special breathing equipment to mitigate such risks. An ethylcellulose coating composition which displays stability at lower pH and which exhibits lower or no ammonia odors would be desirable.

SUMMARY OF THE INVENTION

The instant invention is a process to produce an aqueous dispersion, an aqueous dispersion produced thereby, a pharmaceutical coating composition and a food coating composition comprising the aqueous dispersion.

In one embodiment, the instant invention provides a process to produce an aqueous dispersion comprising feeding ethylcellulose and a dispersant into a melt and mix zone of an extruder wherein the ethylcellulose and dispersant are melted and mixed together to form a melt; conveying the melt to an emulsification zone of the extruder in which the temperature and pressure are controlled; feeding a base and water into the emulsification zone wherein the melt is dispersed to form a high internal phase emulsion; conveying the emulsion to a dilution and cooling zone of the extruder; and feeding water into the dilution and cooling zone to dilute the high internal phase emulsion thereby forming an aqueous dispersion.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

FIG. 1 is a schematic of exemplary equipment for operating the inventive process.

DETAILED DESCRIPTION OF THE INVENTION

The instant invention is a process to produce an aqueous dispersion, an aqueous dispersion produced thereby, a pharmaceutical coating composition and a food coating composition comprising the aqueous dispersion.

The process according to the present invention comprises feeding ethylcellulose polymer and a dispersant into a melt and mix zone of an extruder wherein the ethylcellulose polymer and dispersant are melted and mixed together to form a melt; conveying the melt to an emulsification zone of the extruder in which the temperature and pressure are controlled; feeding a base and water into the emulsification zone wherein the melt is dispersed to form a high internal phase emulsion; conveying the emulsion to a dilution and cooling zone of the extruder; and feeding water into the dilution and cooling zone to dilute the high internal phase emulsion thereby forming an aqueous dispersion.

As used herein, the term high internal phase emulsion refers to an emulsion having equal to or greater than 74 wt % dispersed phase.

Any appropriate base may be used in embodiments of the invention. An exemplary water soluble base is ammonia.

In an alternative embodiment, the instant invention further provides an aqueous dispersion made by any embodiment of the inventive process disclosed herein.

In yet another embodiment, the instant invention further provides a pharmaceutical coating comprising any embodiment of the inventive aqueous dispersion disclosed herein.

In yet another embodiment, the instant invention further provides a modified release coating comprising any embodiment of the inventive aqueous dispersion disclosed herein.

In yet another embodiment, the instant invention further provides a food coating comprising any embodiment of the inventive aqueous dispersion disclosed herein.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that no plasticizer is added into the melt and mix zone of the extruder.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that a plasticizer is added into the melt and mix zone of the extruder.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that a plasticizer is added to the aqueous dispersion. In such instance, the plasticizer may be added at any point following formation of the aqueous dispersion.

Ethylcellulose Polymer

Any ethylcellulose polymer may be used in the invention. Ethylcellulose polymer, as used herein, means a derivative of cellulose in which some of the hydroxyl groups on the repeating glucose units are converted into ethyl ether groups. The number of ethyl ether groups can vary. The United States Pharmacopeia, USP monograph requirement for ethyl ether content is from 44 to 51%. All individual values and subranges from 44 to 51% are included herein and disclosed herein; for example, the ethyl ether content of the ethylcellulose polymer can be from a lower limit of 44, 46, 48 or 50% to an upper limit of 45, 47, 49 or 51%. For example, the ethyl ether content may be from 44 to 51%, or in the alternative, the ethyl ether content may be from 44 to 48%, or in the alternative, the ethyl ether content may be from 48 to 51%, or in the alternative, the ethyl ether content may be from 46 to 50%, or in the alternative, the ethyl ether content may be from 48 to 49.5%.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that the ethylcellulose polymer has a viscosity between 2 and 120 cP. All individual values and subranges are included herein and disclosed herein; for example, the ethylcellulose polymer viscosity can be from a lower limit of 2, 10, 20, 40, 60, 80, 100 or 110 cP to an upper limit of 10, 30, 50, 70, 90, 110 or 120 cP. For example, the ethylcellulose polymer viscosity may be in the range of from 2 to 120 cP, or in the alternative, the ethylcellulose polymer viscosity may be in the range of from 20 to 120 cP, or in the alternative, the ethylcellulose polymer viscosity may be in the range of from 2 to 80 cP, or in the alternative, the ethylcellulose polymer viscosity may be in the range of from 18 to 22 cP, or in the alternative, the ethylcellulose polymer viscosity may be in the range of from 16 to 30 cP. The ethylcellulose polymer has a viscosity, measured as a 5 percent solution in a solvent consisting of 80% toluene and 20% ethanol at 25° C. in an Ubbelohde viscometer.

Commercially available forms of ethylcellulose polymer which may be used in the invention include, for example, those available under the name ETHOCEL, from The Dow Chemical Company. The ethylcellulose polymers used in the inventive examples are commercially available from The Dow Chemical Company as ETHOCEL Standard 10, ETHOCEL Standard 20, or ETHOCEL Standard 100 with ethyl ether content of from 48.0 to 49.5%. Other commercially available ethylcellulose polymers useful in embodiments of the invention include certain grades of AQUALON ETHYLCELLULOSE, available from Ashland, Inc.

In another alternative embodiment, any non-water-soluble cellulose derivative polymer may be used in conjunction with the ethylcellulose polymer.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that the solid phase of the dispersion comprises from 45 to 93 wt % ethylcellulose polymer. All individual values and subranges from 45 to 93 wt % are included herein and disclosed herein; for example, the amount of ethylcellulose polymer in the solid phase of the dispersion can be from a lower limit of 45, 55, 65, 75, 85 or 90 wt % to an upper limit of 50, 60, 70, 80, 90 or 93 wt %. For example, the amount of ethylcellulose polymer in the solid phase of the dispersion may range from 45 to 93 wt %, or in the alternative, the amount of ethylcellulose polymer in the solid phase of the dispersion may range from 45 to 73 wt %, or in the alternative, the amount of ethylcellulose polymer in the solid phase of the dispersion may range from 70 to 93 wt %, or in the alternative, the amount of ethylcellulose polymer in the solid phase of the dispersion may range from 65 to 85 wt %, or in the alternative, the amount of ethylcellulose polymer in the solid phase of the dispersion may range from 70 to 80 wt %.

Dispersant

Any dispersant suitable for the end use of the dispersion may be used. In particular embodiments, the dispersant is selected from the group consisting of saturated and unsaturated fatty acids. Exemplary saturated fatty acids include caprylic acid, capric acid, lauric acid, palmitic acid, myristic acid, stearic acid, and arachidic acid. Exemplary unsaturated fatty acids include myristoleic acid, palmitoleic acid, sapienic acid, oleic acid, linoleic acid, and arachidonic acid.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that the dispersant comprises oleic acid. In yet another alternative embodiment, the instant invention provides a process to produce an aqueous dispersion, an aqueous dispersion, and a coating comprising the aqueous dispersion, in accordance with any of the preceding embodiments, except that the dispersant consists of oleic acid.

"Pure" and "technical grade oleic acid" can be employed as oleic acid. A pure oleic acid is understood as meaning a composition which contains more than 98 wt. % of oleic acid. A "technical grade oleic acid" is understood as meaning a composition which contains oleic acid to the extent of 98 wt. % or less. Such a technical grade oleic acid contains e.g. oleic acid in a range of from 60 to 75 wt. %, linoleic acid in a range of from 5 to 20 wt. % and stearic acid in a range of from 0 to 5 wt. %, based on the total weight of the technical grade oleic acid, the sum of the percentages by weight being 100. Technical grade oleic acid can be obtained from animal fats, for example beef tallow. A technical grade oleic acid with a higher content of oleic acid can likewise be employed, e.g. with 80 to 95 wt. %, preferably 85 to 95 wt. % and furthermore preferably 90 to 95 wt. %, in each case based on the total composition. A technical grade oleic acid with 96 to 98 wt. % of oleic acid, based on the total fatty acid composition, is very particularly preferred. Another technical grade oleic acid with approx. 80 to 90 wt. % of oleic acid, 2 to 10 wt. % of linoleic acid, 2 to 6 wt. % of stearic acid and 2 to 6 wt. % of palmitic acid, based on the total weight of the other technical grade oleic acid, the sum of the percentages by weight being 100.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that the dispersion comprises from 7 to 25 wt % dispersant, based on the weight of the solid phase. All individual values and subranges from 7 to 25 wt % are included herein and disclosed herein; for example, the amount of dispersant, based on the weight of the solid phase, can be from a lower limit of 7, 10, 13, 16, or 20 wt % to an upper limit of 8, 11, 14, 17, 20, or 25 wt %. For example, the amount of dispersant can range from 7 to 25 wt %, based on the weight of the solid phase, or in the alternative, the amount of dispersant can range from 7 to 15 wt %, based on the weight of the solid phase, or in the alternative, the amount of dispersant can range from 7 to 10 wt %, based on the weight of the solid phase, or in the alternative, the amount of dispersant can range from 12 to 25 wt %, based on the weight of the solid phase, or in the alternative, the amount of dispersant can range from 8 to 10 wt %, based on the weight of the solid phase.

Plasticizer

Any plasticizer suitable for the end use of the dispersion may be used. In a particular embodiment, the plasticizer is selected from the group consisting of esters of carboxylic acids. In another embodiment, the plasticizer is a monofunctional carboxylic acid, a multi-functional carboxylic acid or any combination thereof. Exemplary plasticizers include esters of: caprylic acid, capric acid, lauric acid, phthalic acid, citric acid and myristic acid. In a particular embodiment, the plasticizer is dibutyl sebecate.

In yet other embodiments, the plasticizer is selected from the group consisting of triglycerides of vegetable fatty acids. Exemplary vegetable fatty acids include coconut oil, safflower oil, soybean oil and castor oil.

In an alternative embodiment, the dispersion comprises from 0 to 35 wt % plasticizer, based on the weight of the solid phase. All individual values and subranges from 0 to 35 wt % are included herein and disclosed herein; for example, the amount of plasticizer can be from a lower limit of 0, 10, 20, or 25 wt % to an upper limit of 5, 15, 25, or 35 wt %, based on the weight of the solid phase. For example, the amount of plasticizer may be from 0 to 35 wt %, based on the weight of the solid phase, or in the alternative, the amount of plasticizer may be from 0 to 17 wt %, based on the weight of the solid phase, or in the alternative, the amount of plasticizer may be from 17 to 35 wt %, based on the weight of the solid phase, or in the alternative, the amount of plasticizer may be from 10 to 20 wt %, based on the weight of the solid phase, or in the alternative, the amount of plasticizer may be from 15 to 18 wt %, based on the weight of the solid phase.

Process Conditions

The process comprises feeding ethylcellulose and a dispersant into a melt and mix zone of an extruder wherein the ethylcellulose and dispersant are melted and mixed together to form a melt; conveying the melt to an emulsification zone of the extruder in which the temperature and pressure are controlled; feeding a base and water into the emulsification zone wherein the melt is dispersed to form a high internal phase emulsion; conveying the emulsion to a dilution and cooling zone of the extruder; and feeding water into the dilution and cooling zone to dilute the high internal phase emulsion thereby forming an aqueous dispersion.

The general process conditions and equipment which may be used to perform the process are disclosed in U.S. Pat. Nos. 5,539,021 and 5,756,659, the disclosures of which are incorporated herein by reference.

FIG. 1 is a schematic illustrating a particular equipment setup which may be used in one embodiment of the inventive process. The extruder 4 may have several zones, including a mixing and conveying zone 1a, an emulsification zone 1b, and a dilution and cooling zone 1c. Steam pressure at the feed end, which is contained in the mixing and conveying zone, is controlled by placing kneading blocks (not shown) and blister elements (not shown) before the emulsification zone to create a melt seal. Steam pressure at the outlet, which is contained in the dilution and cooling zone, is controlled by using a back-pressure regulator 7. As shown in FIG. 1, the base polymer 3, e.g., ethylcellulose, is fed into the feed throat 2 of the extruder 4 and flows into the mixing and conveying zone 1a. The liquid dispersant and plasticizer, if present, 5 are also fed into the mixing and conveying zone 1a and may be fed separately or jointly. If the dispersant is a solid, it may be optionally fed into the extruder through the extruder feed throat 2. The polymer phase which includes the base polymer, dispersant and plasticizer, if present, combine to form the polymer phase which is melted in the mixing and conveying zone 1a and conveyed down the barrel of the extruder 4 to the emulsification zone 1b.

In the emulsification zone, the polymer phase is combined with an initial amount of water and a base, collectively 6, to create a high internal phase emulsion. The emulsion is then conveyed down the extruder 4 and combined with more water 8 in the dilution and cooling zone to form an aqueous dispersion having less than or equal to 60% wt. solids, e.g. dispersed polymer phase.

Aqueous Dispersion

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that the aqueous dispersion has a pH equal to or less than 12. All individual values and subranges from equal to or less than 12 are included herein and disclosed herein. For example, the pH of the dispersion may be from an upper limit of 12, or in the alternative, the pH of the dispersion may be from an upper limit of 11, or in the alternative, the pH of the dispersion may be from an upper limit of 10, or in the alternative, the pH of the dispersion may be from an upper limit of 9, or in the alternative, the pH of the dispersion may be from an upper limit of 8. In one embodiment, the aqueous dispersion has a pH 8.0 to 9.5.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that the aqueous dispersion has a volume average particle size less than or equal to 1.1 micron. All individual values and subranges of less than or equal to 1.1 microns are included herein and disclosed herein. For example, the volume average particle size may be from an upper limit of 1.1 microns, or in the alternative, the volume average particle size may be from an upper limit of 1.0 micron, or in the alternative, the volume average particle size may be from an upper limit of 0.9 microns, or in the alternative, the volume average particle size may be from an upper limit of 0.8 microns. In one embodiment, the volume average particle size of the aqueous dispersion is from 1.1 micron to 80 nm. In an alternative embodiment, the volume average particle size of the aqueous dispersion is from 1.0 micron to 90 nm.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that the aqueous dispersion has a solids content of equal to or less than 60 wt %. All individual values and subranges from equal to less than 60 wt % are included herein and disclosed herein. For example, the aqueous dispersion may have a solids content of equal to less than 60 wt %, or in the alternative, the aqueous dispersion may have a solids content of equal to less than 55 wt %, or in the alternative, the aqueous dispersion may have a solids content of equal to less than 50 wt %, or in the alternative, the aqueous dispersion may have a solids content of equal to less than 45 wt %, or in the alternative, the aqueous dispersion may have a solids content of equal to less than 40 wt %, or in the alternative, the aqueous dispersion may have a solids content of equal to less than 35 wt %, or in the alternative, the aqueous dispersion may have a solids content of equal to less than 30 wt %. In a particular embodiment, the aqueous dispersion has a solids content of from 25 to 28 wt %. In an alternative embodiment, the aqueous dispersion has a solids content of from 8 to 20 wt %. In an alternative embodiment, the aqueous dispersion has a solids content of from 5 to 35 wt %.

The forces that develop when a dispersion or coating formulation is subjected to a shearing deformation impact the design and composition of the formulation, the coating conditions, and the operational set points of the coating equipment, all which impact the properties of the coated product. The measure of viscometric flow of the dispersion in a cone and plate geometry is a useful indicator of the performance of the dispersion in the coating process. It is preferred to have a low viscosity at a low shear rate. In an alternative embodiment, the instant invention provides a process to produce an aqueous dispersion, an aqueous dispersion, and a coating comprising the aqueous dispersion, in accordance with any of the preceding embodiments, except that the aqueous dispersion has a viscosity at 25° C. and at 1 sec$^{-1}$ of equal to or less than 250 cP. All individual values and subranges from equal to or less than 250 cP are included herein and disclosed herein. For example, the viscosity at 25° C. and at 1 sec$^{-1}$ of the aqueous dispersion can be from an upper limit of 250, 200, 150, 100, 80, 60, 40 or 20 cP.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that the aqueous dispersion comprises 25 wt % solids, has a pH from 10.1 to 10.8 and a viscosity at 1 sec$^{-1}$ of equal to or less than 250 cP at 25° C.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that the aqueous dispersion comprises 25 wt % solids, has a pH from 7.7 to Sand a viscosity at 1 sec$^{-1}$ of equal to or less than 20 cP at 25° C.

Without being bound to any particular theory, the reduced low shear viscosity is presently believed to be a function of the ability of the dispersant to interact with the surface of the ethylcellulose polymer particles. The pulsed field gradient NMR experiment involves applying pulsed magnetic field across the sample to generate a gradient of magnetic field across the sample. This technique has been used traditionally to measure the diffusion coefficients of molecules in solution, as disclosed in the following: Stejskal, E. O.; Tanner, J. E. J. Chem. Phys. 1965, 42 (1), 288. Callaghan, P. *Translational Dynamics and Magnetic Resonance: Principles of Pulsed Gradient Spin Echo NMR*; Oxford University Press: New York, 2011. Price, W. S. *NMR Studies of Translational Motion*; Cambridge University Press: New York, 2009. Wu, D. H.; Chen, A. D.; Johnson, C. S. J. *Magn. Reson., Ser. A* 1995, 115 (2), 260-264.

The pulsed field gradient NMR experiment can be used to determine a diffusion coefficient for the low molecular weight ingredients in the dispersion. Further analysis of the diffusion coefficients can be used to determine how tightly bound the dispersion molecules are to the ethylcellulose particles. The value of the diffusion coefficients determines how tightly the dispersant is bound to the ethylcellulose polymer particles. The presence of multiple diffusion coefficients shows a distribution of locations of dispersant in the dispersion, e.g., on the ethylcellulose polymer particles and free in the aqueous phase.

In an alternative embodiment, the instant invention provides a process to produce an aqueous dispersion, an aqueous dispersion, a pharmaceutical coating comprising the aqueous dispersion, and a food coating comprising the aqueous dispersion in accordance with any of the preceding embodiments, except that at a pH of 10.6, the dispersion exhibits a single diffusion coefficient from $3 \times 10^{-11}$ to $6 \times 10^{-11}$ m$^2$/s. All individual values and subranges from $3 \times 10^{-11}$ to $6 \times 10^{-11}$ m$^2$/s are included herein and disclosed herein; for example, the diffusion coefficient can be from a lower limit of $3 \times 10^{-11}$, $3.5 \times 10^{-11}$, $4 \times 10^{-11}$, $4.5 \times 10^{-11}$, $5 \times 10^{-11}$, or $5.5 \times 10^{-11}$ m$^2$/s to an upper limit of $3.3 \times 10^{-11}$, $3.8 \times 10^{-11}$, $4.3 \times 10^{-11}$, $4.8 \times 10^{-11}$, $5.3 \times 10^{-11}$, or $5.8 \times 10^{-11}$ or $6 \times 10^{-11}$ m$^2$/s.

In an alternative embodiment, the instant invention provides a process to produce an aqueous dispersion, an aqueous dispersion, and a coating comprising the aqueous dispersion, in accordance with any of the preceding embodiments, except that the aqueous dispersion has a pH equal to or less than 10.6 and greater than 8.6 and a single diffusion coefficient.

In an alternative embodiment, the instant invention provides a process to produce an aqueous dispersion, an aqueous dispersion, and a coating comprising the aqueous dispersion, in accordance with any of the preceding embodiments, except that the aqueous dispersion has a low ammonia level as measured by headspace gas chromatography (headspace GC). For example, the aqueous dispersion may have a headspace GC ammonia level of less than or equal to 100 ppm, or in the alternative, the aqueous dispersion may have a headspace GC ammonia level of less than or equal to 90 ppm, or in the alternative the aqueous dispersion may have a headspace GC ammonia level of less than or equal to 80 ppm, or in the alternative the aqueous dispersion may have a headspace GC ammonia level of less than or equal to 70 ppm.

Coating Composition

The aqueous dispersion may be used to make any appropriate pharmaceutical coating composition. Alternatively, the aqueous dispersion may be used to make any appropriate food coating composition. In an alternative embodiment, the coating composition is a delayed release pharmaceutical coating.

EXAMPLES

The following examples illustrate the present invention but are not intended to limit the scope of the invention. All inventive aqueous dispersion examples were made according to the following procedure.

Formation of Aqueous Dispersion

A Berstorff ZE25 twin screw extruder rotating at 450 rpm was used to combine a polymer phase with a water phase to create an ethyl cellulose dispersion. The extruder has a 25 mm screw diameter and a length over diameter (L/D) ratio of 36.

The polymer phase comprised ethyl cellulose, a dispersant, and optionally a plasticizer. The base polymer was delivered to the extruder feed throat by a Schenck Mechatron loss-in-weight feeder. The liquid dispersant and plasticizer were delivered to a mixing and conveying zone injector by Isco syringe pumps.

The polymer phase was then melted and conveyed down the extruder barrel to an emulsification zone where it is combined with an initial amount of water and a base to create a high internal phase emulsion. The base used for all inventive examples was 28% wt. ammonia (as $NH_3$). The emulsion was then conveyed down the extruder barrel to the diluting and cooling zone. The initial water, base, and dilution water are each supplied separately to the extruder with Isco syringe pumps.

Post Addition of Plasticizer

The dispersion of Inventive Example 2 also had dibutyl sebecate plasticizer post added. An appropriate amount of the plasticizer was added to the dispersion to give a solids content of (74/9/17) ETHOCEL STANDARD. 20/oleic acid/dibutyl sebecate. ETHOCEL STANDARD 20 is an ethylcellulose having a viscosity from 18 to 22 cP, which is commercially available from The Dow Chemical Company (DowPharma and Food Solutions division). The plasticizer was then incorporated into the dispersion by mixing at 350 rpm for 45 minutes with an overhead mixer equipped with a propeller blade.

Table 1 provides the components for preparation of Inventive Aqueous Dispersion Examples 1-9 as well as the resultant volume average particle size of the polymer phase in the aqueous dispersion.

TABLE 1

| Inventive Aq. Disp. Ex. | Base Polymer (I) | Dispersant (II) | Plasticizer (III) | Wt. Ratio I/II/III | Particle Size Vmean (μm) |
|---|---|---|---|---|---|
| 1 | ETHOCEL Std. 20 | Oleic acid | Dibutyl sebacate | 74/9/17 | 0.169 |
| 2 | ETHOCEL Std. 20 | Oleic acid | none | 74/9/0 | 0.153 |
| 3 | ETHOCEL Std. 20 | Oleic acid | Dibutyl sebacate | 74/9/17 | 0.380 |
| 4 | ETHOCEL Std. 20 | Oleic acid | Dibutyl sebacate | 74/9/17 | 0.187 |
| 5 | ETHOCEL Std. 10 | Oleic acid | Dibutyl sebacate | 75/8.75/16.25 | 0.186 |
| 6 | ETHOCEL Std. 10 | Oleic acid | Vegetable oil (soybean) | 75/8.75/16.25 | 0.204 |
| 7 | ETHOCEL Std. 100 | Oleic acid | Dibutyl sebacate | 75/8.75/16.25 | 1.05 |
| 8 | ETHOCEL Std. 20 | Oleic acid | Dibutyl sebacate | 74/9/17 | 0.185 |
| 9 | ETHOCEL Std. 20 | Oleic acid | Dibutyl sebacate | 74/9/17 | 0.125 |

Table 2 provides the process flow rates for preparation of Inventive Aqueous Dispersion Examples 1-9.

TABLE 2

| Inventive Aq. Disp. Ex. | Base Polymer | Dispersant | Plasticizer | Initial H₂O | Base | Dilution H₂O |
|---|---|---|---|---|---|---|
| 1 | 41.9 g/min | 5.1 g/min | 9.6 g/min | 11.36 ml/min | 1.68 ml/min | 140 ml/min |
| 2 | 50.55 g/min | 6.15 g/min | 0 g/min | 12.90 ml/min | 1.98 ml/min | 140 ml/min |
| 3 | 41.9 g/min | 5.1 g/min | 9.6 g/min | 11.35 ml/min | 1.68 ml/min | 140 ml/min |
| 4 | 41.9 g/min | 5.1 g/min | 9.6 g/min | 14.60 ml/min | 2.16 ml/min | 140 ml/min |
| 5 | 42.5 g/min | 5.0 g/min | 9.2 g/min | 14.91 ml/min | 1.68 ml/min | 140 ml/min |
| 6 | 42.5 g/min | 5.0 g/min | 9.2 g/min | 14.91 ml/min | 1.68 ml/min | 140 ml/min |
| 7 | 42.5 g/min | 5.0 g/min | 9.2 g/min | 10.53 ml/min | 1.68 ml/min | 140 ml/min |
| 8 | 41.9 g/min | 5.1 g/min | 9.6 g/min | 12.63 ml/min | 2.4 ml/min | 140 ml/min |
| 9 | 41.9 g/min | 5.1 g/min | 9.6 g/min | 7.76 ml/min | 9.95 ml/min | 140 ml/min |

Table 3 provides various measured properties for Inventive Aqueous Dispersion Examples 1-9 as well as for Comparative Aqueous Dispersion Example 1. Comparative Aqueous Dispersion Example 1 was SURELEASE 19020, an aqueous ethylcellulose dispersion which is commercially available from Colorcon, Inc. (Harleysville, Pa.).

TABLE 3

| Aq. Disp. Ex. | pH | % Solids | Brookfield Viscosity (50 rpm, RV# @25° C.) | Particle Size, Vmean (μm) | Headspace GC ammonia (ppm) |
|---|---|---|---|---|---|
| Inv. 1 | 9.07 | 27.84% | 50 cP, RV2 | 0.169 | Not meas. |
| Inv. 2 | 8.96 | 27.99% | 61 cP, RV2 | 0.153 | Not meas. |
| Inv. 3 | 8.76 | 29.21% | 38 cP, RV2 | 0.380 | Not meas. |
| Inv. 4 | 8.71 | 28.23% | 107 cP, RV2 | 0.187 | 70 |
| Inv. 5 | 9.05 | 25.86% | 154 cP, RV1 | 0.186 | Not meas. |
| Inv. 6 | 8.93 | 25.43% | 82 cP, RV1 | 0.204 | Not meas. |
| Inv. 7 | 9.14 | 24.95% | 20 cP, RV1 | 1.05 | Not meas. |
| Inv. 8 | 8.75 | 27.75% | 56 cP, RV2 | 0.185 | Not meas. |
| Inv. 9 | 9.9 | 27.83% | 232 cP, RV3 | 0.125 | Not meas. |
| Comp.1 | 10.6 | 24.47% | 316 cP, RV2 | 0.124 | >600 but <3000 |

Tables 4-6 provide pH and particle size stability testing for Inventive Aqueous Dispersion Example 1 (Table 4), Inventive Aqueous Dispersion Example 3 (Table 5) and Comparative Aqueous Dispersion Example 1 (Table 6). As can be seen by the foregoing examples, the Inventive Aqueous Dispersions exhibit the same stability as the Comparative Aqueous Dispersion while the Inventive Aqueous Dispersions are formed at a lower pH. In contrast, if the pH of the Comparative Aqueous Dispersion 1 is lowered to the range of the Inventive Aqueous Dispersions (e.g., 9.05 or lower), the solids coagulate.

TABLE 4

|  | Particle Size (microns) | pH |
|---|---|---|
| Day one | 0.169 | 9.07 |
| Week 4 | 0.197 | 7.98 |
| Week 6 | 0.190 | 7.94 |
| Week 8 | 0.200 | 7.69 |
| Week 12 | 0.195 | 7.22 |

TABLE 5

|  | Particle Size (microns) | pH |
|---|---|---|
| Day one | 0.380 | 8.76 |
| Week 2 | 0.368 | 7.97 |
| Week 4 | 0.290 | 8.30 |
| Week 6 | 0.353 | 7.99 |
| Week 8 | 0.355 | 7.94 |
| Week 12 | 0.352 | 7.85 |

TABLE 6

|  | Particle Size (microns) | pH |
|---|---|---|
| Day one | 0.124 | 10.6 |
| Week 2 | 0.125 | 9.5 |
| Week 4 | Not measured | Not measured |
| Week 6 | 0.124 | 9.42 |
| Week 8 | 0.125 | 9.50 |
| Week 12 | 0.122 | 9.6 |

Table 7 provides the extruder zone temperatures used in producing each of the Inventive Aqueous Dispersion Examples.

TABLE 7

| Zone | Extruder Temperature Setpoint (° C.) |
|---|---|
| 2 | 30 |
| 3 and 4 | 130 |
| 5 | 140 |
| 6 | 140 |
| 7 | 140 |
| 8 | 140 |
| 9 | 140 |

Diffusion Coeffcients

The experiments were performed using pulsed field gradient NMR using the longitudinal eddy-current delay experiment with bipolar pulse pairs to reduce artifacts arising from eddy current and phase distortions. The intensity decay curves are fitted with the empirical formula $[I/I_o = \exp[-D(\gamma g \delta)^2 (\Delta - \delta/3)]$ to obtain the diffusion coefficient, D. Where; I is intensity, $\gamma$=magnetogyric ratio of H, $\delta$=gradient time, g=gradient strength, $\Delta$=diffusion time. In the current experiment, the diffusion delay time was kept at 100 ms and gradient was applied for 12 ms and incremented to 53 G/cm in 16 steps. 32 scans per increment were taken for ample signal to noise with a recycle delay time of 5 s. Samples were diluted to 15% solids for the NMR analysis. Table 8 shows the diffusion coefficients obtained by this method.

TABLE 8

|  | pH | Diffusion coefficient (m²/s) |
|---|---|---|
| Inventive Aqueous Dispersion Example 4 | 10.6 | $4.4 \times 10^{-11}$ |
| Comparative Aqueous Dispersion 1 | 10.6 | $2.6 \times 10^{-10}$ and $3.6 \times 10^{-11}$ |

As can be seen from the foregoing examples, the Comparative Aqueous Dispersion exhibits two diffusion coefficients wherein one is an order of magnitude higher indicating free dispersant in the dispersion. In contrast, Inventive Aqueous Dispersion Example 4 exhibits a single diffusion coefficient that which indicates all surfactants are equally interacting with the particles and there is no free dispersant in the aqueous phase. The increased amount of free dispersant in the water phase is responsible for the increase in low shear viscosity of samples of the current art. For the samples of the invention at pH 8.6 a wider distribution of diffusion coefficients was observed indicating that some of the dispersant is very tightly bound to the ethylcellulose particles and the rest is loosely bound at the interface or free in the water phase. Samples of the current art coagulate at pH 8.6, therefore NMR measurements could not be done for that dispersion at the lower pH.

The measure of viscometric flow of the dispersion in a cone and plate geometry is a useful indicator of the performance of the dispersion in the coating process. Table 9 shows the reduced low shear viscosity of the Inventive Examples compared to the Comparative Example.

TABLE 9

Cone and plate steady shear viscosity table

|  | pH | Particle size (µm) | Shear rate (sec⁻¹) | Viscosity (cP) |
|---|---|---|---|---|
| Inv. Aq. Disp. Ex. 3 | 7.87 | 0.38 | 1 | 9.9 |
| Inv. Aq. Disp. Ex. 3 | 10.24 | 0.38 | 1 | 41.1 |
| Inv. Aq. Disp. Ex. 4 | 8.22 | 0.179 | 1 | 13.7 |
| Inv. Aq. Disp. Ex. 4 | 10.26 | 0.179 | 1 | 168 |
| Comp. Aq. Disp. Ex. 1 | 10.27 | 0.124 | 1 | 1875 |

Preparing Drug Layered Sugar Spheres:

Sugar spheres (20/25 mesh) were powder drug layered with micronized Chlorpheniramine Maleate (CPM) using a VFC-Lab 3 fluid bed with a GXR-35 rotor insert from Freund Vector. A binder solution of 5 weight % METHOCEL E5 was used. The targeted dosage was 12 mg CPM per 100 mg of drug layered beads. The process parameters were as follows: slit airflow=12 CFM, slit air temperature=50° C., rotor speed=250 rpm, pump speed=10 rpm, pump rate=7.5 g/min, nozzle air=20 psi, drying airflow=60 CFM, drying air temp=60° C., powder feed rate=10 g/min, product temperature=23 to 25° C. and the bead batch size=5000 grams.

Applying Controlled Release Coating to Drug Layered Sugar Spheres:

The drug layered sugar spheres were coated in a fluidized bed coater (VFC-Lab 3, Wurster 4 liter insert with a 6 inch column from Freund Vector) using the aqueous EC dispersions, diluted to 15% solids. The starting batch size was 1 kg, with a targeted weight gain of 20%.

The process parameters were as follows: inlet air temperature setpoint=60-65° C., actual product temperature=31-44°, exhaust air temperature=32-44° C., air flow=40-42 CFM, spray rate=11-17 g/min, nozzle air=20 psi, spray nozzle diameter=1.2 mm, and Wurster column gap=0.5 inches. The beads were circulated in the column for 10 min, and then cured in an oven at 60° C. for 2 hours.

TEST METHODS

Test methods include the following:

Viscosity

Ethylcellulose Polymer:

viscosity is measured as a 5 percent solution in a solvent consisting of 80% toluene and 20% ethanol at 25° C. in an Ubbelohde viscometer.

Dispersion:

The viscosity of the dispersion was measured with a Brookfield Model DV-II+ viscometer with the given RV spindle number spinning at a temperature of 50 C.

Cone & Plate:

Rheology measurements were performed with an Anton Paar MCR 301 rheometer in the automated mode. In this mode, a six-axis robot aspirates and dispenses the sample with 2.5 mL Eppendorf syringes while another one cleans the measuring system. All sample solids were adjusted to 25% and the measurements were carried out at 25° C. using a cone and plate geometry with 50 mm diameter and 0.5° cone angle with a sample size of 375 µL. After equilibration for 2 minutes, a steady state flow test was performed from 1 to 10,000 s−1 shear rates where 6 measurement points were collected per decade with logarithmically varying measurement point durations starting from 90 s at the lowest shear rate and going down to 30 s at the highest.

Stability

The stability data generated above was generated from samples stored in sealed glass jars at 50° C. in a temperature controlled oven without controlled humidity. At each time point the sample was opened, the pH and particle size was measured, and the sample was placed back into the 50° C. temperature controlled oven.

Particle Size

Volume average particle size was measured by light scattering using a Beckman Coulter LS 230 Laser Light Scattering Particle Sizer (Beckman Coulter Inc., Fullerton, Calif.).

Headspace Ammonia Measurement

Draeger gas detection tubes (5-100 ppm part number 8101942, 5-600 ppm part number CH20501, 0.5-10 volume percent CH31901) were used to measure the ammonia in the headspace over the Inventive and Comparative Aqueous Dispersions. A 3 liter TEDLAR (polyvinyl fluoride) bag was filled with nitrogen gas. 1.0 mL of sample was added and allowed the sample to equilibrate for 80 min. Then 100 mL of the vapor in this bag was passed through a Draeger tube using a hand pump. The results are reported as vapor phase concentration of ammonia in ppm. A water blank gave a result of no ammonia detected (5-100 ppm tube). The sample prepared using comparative aqueous dispersion example 1 completely saturated the 5-600 ppm tube, but did not register on the 0.5-10 volume percent tube.

Dissolution Testing:

Dissolution testing was done with a Distek D12571994 dissolution system with a Hewlett-Packard CN 02501855 Diode Array Spectrophotometer. Large cells (10.0 mm) were used in the spectrophotometer. The wavelength used for Chlorpheniramine Maleate was 262 nm. All dissolutions were done in 900 mL deaerated DI water (Distek MD-1 De-Gasser) in standard vessels. The media temperature was 37±0.5° C. and USP Apparatus I was used (basket) with a rotation speed of 100 rpm. Six samples were run for each dissolution test.

The present invention may be embodied in other forms without departing from the spirit and the essential attributes thereof, and, accordingly, reference should be made to the appended claims, rather than to the foregoing specification, as indicating the scope of the invention.

We claim:

1. A process to produce a dispersion comprising:
    feeding ethylcellulose polymer into a melt and mix zone of an extruder via a feed throat,
    feeding a liquid dispersant selected from saturated and unsaturated fatty acids into the melt and mix zone of the an extruder via a pump, wherein
    the ethylcellulose polymer and dispersant are melted and mixed together to form a melt;
    conveying the melt to an emulsification zone of the extruder in which the temperature and pressure are controlled;
    feeding a base and water into the emulsification zone wherein the melt is dispersed to form a high internal phase emulsion;
    conveying the emulsion to a dilution and cooling zone of the extruder; and
    feeding water into the dilution and cooling zone to dilute the high internal phase emulsion thereby forming an aqueous dispersion.

2. The process according to claim 1, comprising feeding ethylcellulose polymer and the dispersant in the absence of a plasticizer into the melt and mix zone of the extruder.

3. The process according to claim 1, further comprising: adding a plasticizer into the melt and mix zone of the extruder.

4. The process according to claim 1, further comprising: adding a plasticizer to the aqueous dispersion.

5. The process according to claim 3, wherein the plasticizer is selected from the group consisting of esters of carboxylic acids.

6. The process according to claim 1, wherein the ethylcellulose has a viscosity between 2 and 120 cP.

7. The aqueous dispersion produced by the process of claim 1.

8. The aqueous dispersion according to claim 7, wherein the aqueous dispersion has a pH equal to or less than 12.

9. The aqueous dispersion according to claim 7, wherein the aqueous dispersion has a pH 8.0 to 9.5.

10. The aqueous dispersion according to claim 7, wherein the aqueous dispersion has an volume average particle size less than or equal to 1.1 micron.

11. The aqueous dispersion according to claim 7, wherein the aqueous dispersion has a solids content of equal to or less than 35 wt %.

12. The aqueous dispersion according to claim 7, wherein the aqueous dispersion comprises 25 wt % solids, has a pH from 10.4 to 10.8 and a viscosity at 1 sec$^{-1}$ of equal to or less than 100 cp at 25° C.

13. The aqueous dispersion according to claim 7, wherein the aqueous dispersion comprises 25 wt % solids, has a pH from 8.5 to 9 and a viscosity at 1 sec$^{-1}$ of equal to or less than 20 cp at 25° C.

14. The aqueous dispersion according to claim 7, wherein the aqueous dispersion at pH of 10.6 exhibits a single diffusion coefficient, D, between $3 \times 10^{-11}$ and $6 \times 10^{-11}$ m$^2$/s.

15. A pharmaceutical coating composition comprising at least one aqueous dispersion according to claim 7.

16. A food coating composition comprising at least one aqueous dispersion according to claim 7.

* * * * *